Figure 1:
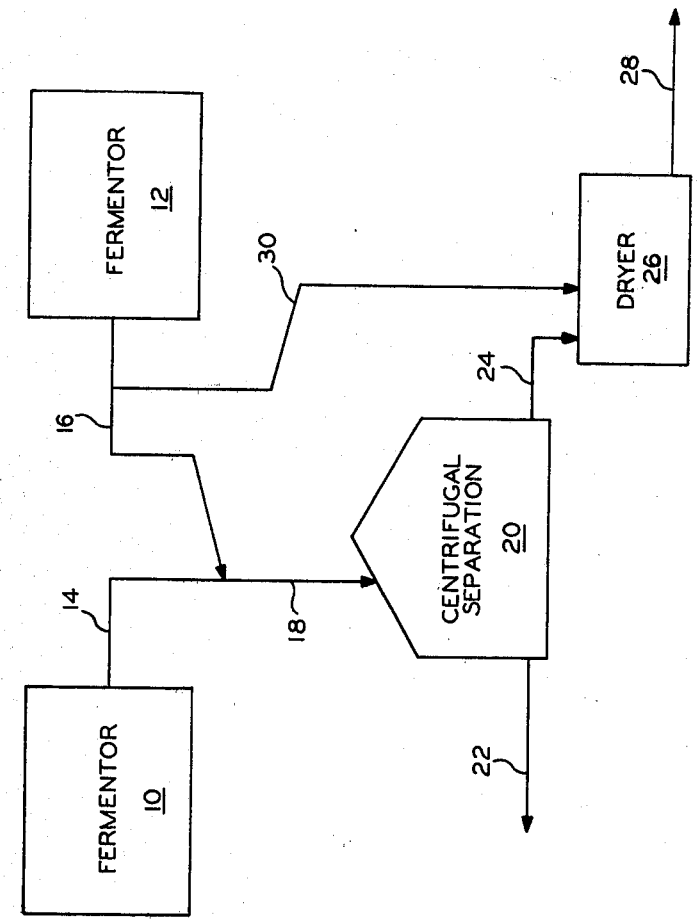

United States Patent [19]

Vanderveen et al.

[11] 4,399,223

[45] Aug. 16, 1983

[54] CELLULAR PRODUCT SEPARATION

[75] Inventors: John W. Vanderveen; Donald O. Hitzman; Eugene H. Wegner, all of Bartlesville, Okla.

[73] Assignee: Phillips Petroleum Company, Bartlesville, Okla.

[21] Appl. No.: 280,960

[22] Filed: Jul. 7, 1981

[51] Int. Cl.$^3$ .............................................. C12N 1/02
[52] U.S. Cl. ................................... 435/261; 210/730; 210/787; 435/803
[58] Field of Search ............... 435/243, 253, 261, 803; 426/495, 656; 210/730, 778, 787

[56] References Cited

U.S. PATENT DOCUMENTS

| | | |
|---|---|---|
| Re. 29,130 | 2/1977 | Lee et al. ...................... 435/261 X |
| 3,407,934 | 10/1968 | Ejefors ............................ 435/261 X |
| 3,738,488 | 6/1973 | Hondermark .................. 435/261 X |
| 3,798,320 | 3/1974 | Weiss et al. ............................ 424/92 |
| 3,846,244 | 11/1974 | Dew et al. .................... 435/261 X |
| 3,958,038 | 5/1976 | Hitzman ............................ 426/656 |
| 3,970,518 | 7/1976 | Giaever .......................... 435/261 X |
| 4,105,804 | 8/1978 | Terui et al. ........................ 426/656 |

OTHER PUBLICATIONS

Levich, V. G., "Impaction of Aerosols and Colloids", Physicochemical Hydrodynamics, Prentice-Hall, Inc., Englewood Cliffs, N.J., 1962, pp. 221-226.

*Primary Examiner*—Robert A. Yoncoskie

[57] ABSTRACT

The separation of a first cellular product comprising relatively small cells from a first liquid by centrifugal separation is facilitated by addition to the first liquid of a second cellular material comprising relatively larger cells.

8 Claims, 2 Drawing Figures

CELLULAR PRODUCT SEPARATION

This invention relates to the production of microorganisms by fermentation processes. This invention further relates to the recovery of microorganisms from a fermentation liquid by centrifugation. This invention further relates to the recovery of bacteria produced by fermentation and processed by centrifugation of the fermentation liquids. This invention further relates to the recovery of bacteria by centrifugation using other microorganisms to aid bacteria collection by impaction or by hydrodynamic capture.

Microorganisms commonly used for production of proteins by fermentation processes fall into two broad categories, bacteria and yeast. Bacteria have an inherently faster growth rate and produce a product with higher protein content. Yeast cells, however, are considerably larger in size (generally about 4-10 microns) compared to bacteria (generally about 0.1 to 4.0 microns). Thus, although bacteria have more desirable growth properties, they are more difficult to recover from the fermentation broth.

Means used to separate microorganisms from fermentation liquids heretofore used include centrifugation, small pore filtration, freezing, coagulation by use of acids, flocculation by heating and the like. Each of these methods has certain disadvantages. Centrifugation is usually relatively ineffective for bacteria. The use of small pore filters results in slow filtration and generally low cake capacity for a given filter. Freezing involves considerable additional processing expense to achieve separation of the cells. The use of additional chemicals to cause coagulation has the disadvantage that undesirable contaminating materials may be added to the finished protein supplement material. Heating to cause flocculation also involves considerable additional processing expense to achieve separation of the cells. Frequently, chemical (i.e. acid addition) and physical (i.e. heating or freezing) processes employed to aid coagulation or flocculation are found to cause significant cell fragmentation and solubilization, thus reducing the protein recovery possible in subsequent operations, such as centrifugation or filtration.

Accordingly, an object of this invention is to provide a method and apparatus for the production of microorganisms by fermentation processes. An additional object of the invention is to provide a method and apparatus for the recovery of microorganisms from a fermentation liquid by centrifugation. An additional object of the invention is to provide a method and apparatus for the recovery of bacteria produced by fermentation and processed by centrifugation of the fermentation liquids. Another object of the invention is to provide a method and apparatus for recovery of bacteria by centrifugation using other microorganisms to aid bacteria collection by impaction or hydrodynamic capture.

In accordance with the present invention, bacteria are made amenable to recovery by centrifugal means. Two fermentation streams, comprising 1-99% by volume (v/v) yeast fermentation liquor, preferably 10-90% (v/v) yeast fermentation liquor, more preferably 10-50% (v/v) yeast fermentation liquor, and the remainder bacteria fermentation liquor are thoroughly mixed and subjected to conventional centrifugal means.

The larger yeast particles aid collection of the smaller bacteria particles by the phenomenon of impaction. The larger yeast particles move through the rotational field faster than the bacteria particles. As the yeast particles overtake the bacteria particles, the bacteria particles are swept along by hydrodynamic capture. The efficiency of this capture, E, for a single yeast particle encountering a substantially smaller single bacterial particle is a function of the size differential for the particles involved and can generally be expressed as $$E = 3r/R$$

where
r = diameter of bacteria particle
R = diameter of yeast particle Thus, the predicted efficiency of bacteria capture can be readily determined if the typical size of the bacteria and yeast particles involved is known. For example, the efficiency of bacteria recovery by hydrodynamic capture for bacteria with a diameter of about 0.5 microns and yeast cells with a diameter of about 5 microns is calculated to be about 30%. Collection efficiency will of course decrease as bacteria cells of smaller size are employed or if larger yeast cells are employed while collection efficiency should increase as larger bacteria particles are employed, and as the difference between the yeast/bacteria size decreases. Collection efficiency will also increase as the proportion of yeast cells to bacteria cells increase thereby increasing the statistical probability that each bacteria cell will have more opportunity to be impacted by one or more yeast cells.

Additional objects and advantages of the invention will be apparent from consideration of the drawings in which the two figures are alternative schematic illustrations of a fermentation process and apparatus of the invention.

Referring to FIG. 1 in detail, there is illustrated a bacterial fermentation zone 10 comprising suitable apparatus known in the art and operated under conditions for growing a bacterial cellular product such as bacterial single cell protein (SCP). A yeast fermentation zone 12 is similarly provided for producing a product containing cellular yeast material such as yeast SCP. The effluent liquid product stream 14 from the bacterial fermentation zone 10 is a bacteria-containing fermentation liquid from which separation of bacterial cells must be accomplished to obtain the bacterial SCP product. Similarly, the yeast-containing fermentation liquid effluent stream 16 from the yeast ferementation zone 12 contains yeast cells to be separated from the fermentation liquid in which they are contained.

In order to provide a mixed product liquid containing both yeast and bacteria cells in which the yeast cells can be utilized in hydrodynamic capture of bacterial cells, the bacteria-containing fermentation liquid in effluent stream 14 is combined with the yeast-containing fermentation liquid from effluent stream 16 to form a mixed product liquid stream 18. The mixed product liquid stream 18 is introduced into a centrifugal separation zone 20 which can be any suitable apparatus comprising centrifugal separation means. A liquid separation effluent stream 22 comprising fermentation liquid from the bacterial fermentation zone and the yeast fermentation zone is removed from the centrifugal separation zone to be disposed of or recycled as appropriate. A cellular product material containing mixed bacteria and yeast cells is conveyed from the centrifugal separation zone 20 by a product conduit 24 for appropriate product processing such as drying in a dryer 26. The dried cellular product is then removed by suitable means 28 for further processing and use as a source of protein.

Depending on the relative capacities of the bacterial fermentation zone 10 and the yeast fermentation zone 12 as well as the relative cell densities in the bacteria-containing fermentation liquid stream 14 and the yeast-containing fermentation liquid effluent stream 16, use of the entire effluent from the yeast fermentation zone 12 to aid in centrifugal separation of the effluent from the bacterial fermentation zone 10 may not be necessary. It is therefore within the scope of the invention to process a portion of either the bacteria-containing fermentation liquid or the yeast-containing fermentation liquid separately by other known means. Since, however, use of the generally larger yeast cells to assist in hydrodynamic capture of the generally smaller bacteria cells during centrifugal separation is particularly advantageous in the separation of bacterial cells from a fermentation broth, in the presently preferred embodiment of the invention, substantially the entire effluent from the bacterial fermentation zone 10 is combined with at least a portion of the effluent from the yeast fermentation zone 12 so that the mixed product liquid stream 18 contains a sufficient proportionate amount of yeast cell content to result in hydrodynamic capture of at least a substantial portion of the bacteria during centrifugal separation.

If the entire yeast fermentation zone effluent is not required for this purpose, the remainder may be subjected to other appropriate recovery techniques. For example, if the yeast fermentation zone 12 is adapted to produce a high cell density product which can be subjected to direct drying without previous liquid separation, a second effluent stream 30 from the yeast fermentation zone 12 comprising material not required to assist in the centrifugal separation of bacterial product can be passed directly to the dryer 26.

Figure 2:
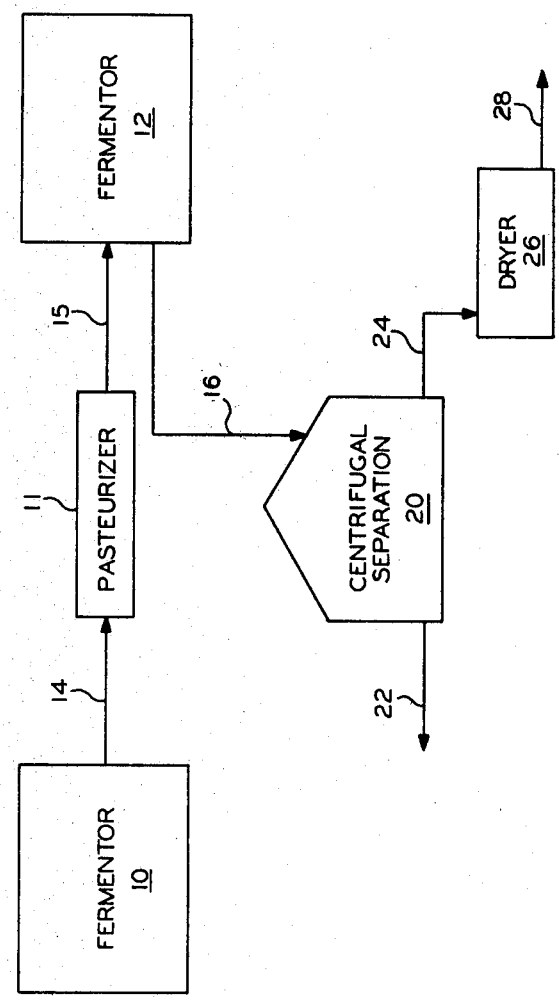

Referring to FIG. 2 in detail, there is illustrated an alternate embodiment wherein the effluent liquid product stream 14 from the first fermentation zone 10 is passed into pasteurizer 11 where the microognism products of the first fermentation are rendered non-viable before passing into the second fermentation zone 12 via conduit 15. The product stream 16 from fermentor 12 comprises a mixture of the relatively small microorganism product from fermentor 10 and the relatively large microorganism product of fermentor 12 which is then subjected directly to centrifugal separation.

Effluent stream 22 and product stream 24 from the centrifugal separation step are then treated as described above.

The fermentation processes carried on within the bacterial fermentation zone 10 and the yeast fermentation zone 12 can be any suitable processes which produce bacterial and yeast products having relative sizes capable of providing useful assistance in the centrifugal separation of bacterial cells caused by the phenomenon of impaction or hydrodynamic capture by the larger yeast cells. In this respect, the ratio of the diameter of yeast cells produced in the fermentation zone 12 to the diameter of bacteria cells produced in the bacterial fermentation zone 10 will ordinarily be within the range of from about 100:1 to about 1:1. More commonly, this ratio can be expected to be within the range of from about 50:1 to about 2:1. For most efficient capture of bacterial cells, it is preferred that the ratio be less than about 20:1, and a ratio of less than about 10:1 is most preferred. Even when the ratio of the diameter of yeast cells to bacteria cells is relatively high, however, the efficiency of separation of the bacterial cells can be significantly improved by the addition of appropriately greater number of yeast cells to the mixed product containing liquid.

The particular bacterial and yeast microorganisms utilized in the fermentation processes can be any combination which provide a desirable size and separation characteristic relationship as well as a desirable product quality relationship. The nutrient feedstocks to the separate fermentation zones can be the same or different and can be either closely related or not. For example, one of the fermentation zones may use a hydrocarbon nutrient feedstock while the other may use, for example, an alcohol nutrient feedstock. However, in the interest of efficient operation of the bacterial and yeast fermentation processes as a unit, particularly if recycle of the liquid centrifugal separation zone effluent stream 22 to one or both of the processes is desired or if the embodiment of FIG. 2 is used, use of the same or compatible nutrient systems is presently preferred when possible.

Suitable microorganisms employed in the practice of the present invention can be hydrocarbon assimilating yeasts or bacteria. Suitable hydrocarbon assimilating bacteria include species of the genera Psuedomonas, Bacillus, Flavobacterium and Sarcina. Illustrative species of these genera are *P. aeruginosa, P. oleovorans, P. putida, P. borepolis, P. methanica, P. fluorescens, P. pyocyanea, B. aureus, B. acidi, B. subtilis, B. urica, B. cereus, B. coagulans, B. mycoides, B. circulans, B. megaterium, Flavobacterium aquatile, Sarcina alba,* and *Sarcina luteum.* Other preferred genera are Achromobacter and Nocardia, as illustrated by species such as *A. xerosis, A. agile, A. gutatus, A. superficialis, A. parvulus, A. cycloclastes, N. salmonicolor, N. asteroides, N. minimus, N. opaca, N. corallina, N. rubra,* and *N. paraffinae.* The genus Mycobacterium is useful, particularly such species as *M. paraffinicum, M. phlei, M. lacticola, M. rhodochrous, M. smegmatis, M. rubrum, M. luteum, M. album,* and *M. byalinicum.*

Still other hydrocarbon-utilizing bacteria are *Methanomonas methanica,* Methanomonas sp., *Micrococcus paraffinae, B. aliphaticum, B. hidium, B. benzoli,* and species of Micromonospora. Other useful genera include Brevibacterium, Aerobacter, and Corneybacterium.

Of the yeasts, the preferred hydrocarbon assimilating organisms are of the family Cryptococcaccae, and, particularly, of the subfamily Cryptococcoidae. Preferred genera are Pichia, Torulopsis (or Torula), and Candida. Preferred species are *Pichia polymorpha, Candida lipolytica, Candida pulcherrima, Candida utilis, Candida utilis Var. major, Candida tropicalis, Candida intermedia,* and *Torulopsis colliculosa.* Other useful species are *Hansenula anomala, Oidium lactia,* and *Neurospora sitophila.*

The hydrocarbon used with such hydrocarbon assimilating organisms can be one that is liquid at the temperature of growth of the microorganisms. Aliphatic hydrocarbons are preferred, and these may be saturated or unsaturated, straight or branched chain, and having up to 20 or 30 or 40 or more carbon atoms. Saturated straight chain hydrocarbons containing 12 or more carbon atoms are particularly desirable. Cyclic hydrocarbons, comprising aromatic and alicyclic compounds, are also of use, including alkyl-substituted cyclic compounds having 1, 2, or more alkyl substituents, each of any suitable length, chain configuration, and degree of unsaturation, and in which the cyclic moiety is aromatic or cycloparaffinic. Alkyl-substituted aromatic hydrocarbons include toluene, the various xylenes, mesitylene, ethyl benzene, p-cymene, the diethylbenzenes, and the isomeric propylbenzenes, butylbenzenes, amylbenzenes, heptylbenzenes, and octylbenzenes. Among the useful alkyl-substituted cycloparaffins are methylcyclopentane, the di- and trimethylcyclopentanes, ethylcyclopentane, the diethylcyclopentanes, the various propyl-, butyl-, amyl-, hexyl-, and octylcyclopentanes. There may be also used the alkylcyclohexanes, which are substituted in a manner corresponding to the former alkylcyclopentanes, as well as such compounds as the various tetramethylcyclohexanes, methylethylcyclohexanes, methylpropylcyclohexanes, and the like. Crude oils, various petroleum fractions, and redidua are also of use.

It will be appreciated that the hydrocarbon may be liquid not only by having a suitable melting point but also be being dissolved in a suitable solvent. The hydrocarbons contemplated in the preceding paragraphs are those which are normally liquid at temperatures of growth of the microorganisms. However, other useful hydrocarbons are those which are normally gaseous at these temperatures, such as methane, ethane, propane, butane and other $C_3$ to $C_5$ hydrocarbons. These gaseous hydrocarbons may be dissolved in a normally liquid hydrocarbon, such as a petroleum fraction in the gasoline or kerosene boiling range, or in an alkane like octane, nonane, or decane. Also, normally, solid hydrocarbons may be used as the source of carbon by dissolving them in a hydrocarbon solvent, in the manner described.

These microorganisms are preferably cultured in various mixtures of mineral salts dissolved in water with the hydrocarbon as the sole carbon source. Generally, a suitable medium should have (a) a balanced mineral content, (b) a nitrogen source such as ammonium or nitrate ions, (c) pH near neutrality, and, optionally (d) oxygen. Exceptions are known to each of these conditions. For example, some hydrocarbon utilizing organisms are capable of fixing elemental nitrogen, thus eliminating the need for an added nitrogen source. As another example, oxygen is not required in the growth and development of many hydrocarbon utilizing organisms, such as facultative anaerobic species. For a more complete discussion of suitable conventional aqueous media that can be employed in the fermentation of hydrocarbons, reference is made to Petroleum Microbiology by Beerstecher, Elsevier Press, Inc., 1954.

The fermentation can also be carried out with a straight chain alcohol having from 1 to 16 carbon atoms per molecule. This feedstock is also assimilable by many types of microorganisms and supplies the carbon and energy for the microbial growth. Preferably the alcohol has from 1 to 6 carbon atoms per molecule and more preferably the alcohol will be either ethanol or methanol and most preferably, methanol. Examples of suitable alcohols include methanol, ethanol, 1-propanol, 1-butanol, 1-octanol, 1-dodecanol, 1-hexadecanol, 2-propanol, 2-butanol, 2-hexanol and the like. Mixtures of alcohols can also be employed if desired.

The microorganisms which can be used in the fermentation process and are capable of assimilating one or more of the above alcohols as the source of carbon and energy in the growth or propagation of the microorganisms can be selected from bacteria or yeast.

Suitable alcohol assimilating yeasts include species from the genera Candida, Hansenula, Torulopsis, Saccharomyces, Pichia, Debaryomyces, Lipomyces, Cryptococcus, Nematospora, and Brettanomyces. The preferred genera include Candida, Hansenula, Torulopsis, Pichia, and Saccharomyces. Examples of suitable species include:

Candida boidinii
Candida mycoderma
Candida utilis
Candida stellatoidea
Candida robusta
Candida claussenii
Candida rugosa
Brettanomyces petrophiium
Hansenula minuta
Hansenula saturnus
Hansenula californica
Hansenula mrakii
Hansenula silvicola
Hansenula polymorpha
Hansenula wickerhamii
Hansenula capsulata
Hansenula glycozyma
Hansenula henricii
Hansenula nonfermentans
Hansenula philodendra
Torulopsis candida
Torulopsis bolmii
Torulopsis versatilis
Torulopsis glabrata
Torulopsis molishiana
Torulopsis nemodendra
Torulopsis nitrotaphila
Torulopsis pinus
Torulopsis sonorensis
Pichia farinosa
Pichia polymorpha
Pichia membranefaciens
Pichia pinus
Pichia pastoris
Pichia trehalophila
Saccharomyces cerevisiae
Saccharomyces fragilis
Saccharomyces rosei
Saccharomyces acidifaciens
Saccharomyces elegans
Saccharomyces rouxii
Saccharomyces lactis
Saccharomyces fractum Suitable alcohol assimilating bacteria include species from the genera Bacillus, Mycobacterium, Actinomyces, Nocardia, Pseudomonas, Methanomonas, Protaminobacter, Methylococcus, Arthrobacter, Methylomonas, Brevibacterium, Acetobacter, Micrococcus, Rhodopseudomonas, Corynebacterium, Microbacterium, Achromobacter, Methylobacter, Methylosinus, and Methylocystis. Preferred genera include Bacillus, Pseudomonas, Protaminobacter, Micrococcus, Arthrobacter and Corynebacterium.

Examples of suitable species include:
Bacillus subtilus
Bacillus cereus
Bacillus aureus
Bacillus acidi
Bacillus urici
Bacillus coagulans
Bacillus mycoides
Bacillus circulans
Bacillus megaterium Bacillus licheniformis
i Pseudomonas methanolica
Pseudomonas ligustri
Pseudomonas orvilla
Pseudomonas methanica
Pseudomonas fluorescens
Pseudomonas aeruginosa
Pseudomonas oleovorans
Pseudomonas putida
Pseudomonas borepolis
Pseudomonas pyocyanea
Pseudomonas methylphilus
Pseudomonas brevis
Pseudomonas acidovorans
Pseudomonas methanoloxidans
Pseudomonas aerogenes
Protaminobacter ruber
Corynebacterium simplex
Corynebacterium hydrocarbooxydans
Corynebacterium alkanum
Corynebacterium oleophilus
Corynebacterium hydrocarboclastus
Corynebacterium glutamicum
Corynebacterium viscosus
Corynebacterium dioxydans
Corynebacterium alkanum
Micrococcus cerificans
Micrococcus rhodium
Arthrobacter rufescens
Arthrobacter parafficum
Arthrobacter simplex
Arthrobacter citreus
Methanomonas methanica
Methanomonas methanooxidans
Methylmonoas agile
Methylomonas albus
Methylomonas rubrum
Methylomonas methanolica
Mycobacterium rhodochrous
Mycobacterium phlei
Mycobacterium brevicale
Nocardia salmonicolor
Norcardia minimus
Norcadia corallina
Norcardia butanica
Rhodopsuedomonas capsulatus
Microbacterium ammoniaphilus
Achromobacter coagulans
Brevibacterium butanicum
Brevibacterium roseum
Brevibacterium flavum
Brevibacterium lactofermentum
Brevibacterium paraffinolyticum
Brevibacterium ketoglutamicum
Brevibacterium insectiphilium The growth of the microorganisms is sensitive to the operating temperature of the fermentor and each particular microorganism has an optimum temperature for growth. The broad temperature range employed for the fermentation process of this invention is from about 30 degrees C. to about 65 degrees C. and more preferably between about 35 degrees C. and about 60 degrees C. The temperature selected will generally depend upon the particular microorganism(s) employed in the process since they will each have a somewhat different temperature/growth rate relationship.

A suitable nutrient medium is supplied to the fermentor to provide nutrients such as an assimilable source of nitrogen, phosphorus, magnesium, calcium, potassium, sulfur and sodium as well as trace quantities of copper, manganese, molybdenum, zinc, iron, boron, iodine and selenium. As is well known in the art of fermentation, the relative amounts of the above nutrients can vary depending on the microorganisms selected for the process. In addition, the nutrient medium can also contain vitamins as is known in the art when their presence is known to be desirable for the propagation of certain microorganisms. For example, many yeasts appear to require the presence of one or both of the vitamins biotin and thiamin for their propagation. A typical example of a suitable nutrient medium is as follows:

| One Liter Aqueous Solution | |
|---|---|
| Component | Amount |
| $H_3PO_4$ (85%) | 2.0 mL |
| KCl | 1.0 g |
| $MgSO_4.7H_2O$ | 1.5 g |
| $CaCl_2.2H_2O$ | 0.2 g |
| NaCl | 0.1 g |
| Trace Mineral Solution | 5.0 mL |

The trace mineral solution as listed in the above recipe is formulated as given in the recipe below:

| One Liter Aqueous Solution (Trace Mineral Solution) | |
|---|---|
| Component | Amount |
| $CuSO_4.5H_2O$ | 0.06 g |
| KI | 0.08 g |
| $FeCl_3.6H_2O$ | 4.80 g |
| $MnSO_4.H_2O$ | 0.30 g |
| $Na_3MoO_4.2H_2O$ | 0.20 g |
| $ZnSO_4.7H_2O$ | 2.00 g |
| $H_3BO_4$ | 0.02 g |

When using the nutrient medium described above the source of assimilable nitrogen is supplied by the separate addition of aqueous ammonia ($NH_4OH$) to the fermentation vessel. The amount of $NH_4OH$ added will depend upon the pH desired for the reaction mixture. Without any added $NH_4OH$ the pH will be about 2, for the nutrient medium. For the utilization of yeasts in the fermentation process the pH is preferably in the range of about 3 to about 5 and for the utilization of bacteria the pH should preferably be in the range of about 6 to about 7.5.

The fermentation reaction is an aerobic process wherein the oxygen needed for the process can be supplied from a free oxygen-containing source such as air which is suitably supplied to the fermentation vessel at a pressure of from about 1 to about 100 atomospheres and preferably from about 1 to about 10 atmospheres. One good source of oxygen is oxygen enriched air. The fermentation reaction is often favorably affected by use of pressure within the above-described broad and preferred ranges.

The fermentation process can be carried out as a continuous or as a batch process. In the continuous or batch process modes of operation the fermentation reactor is first sterilized and subsequently inoculated with a culture of the desired microorganisms in the presence of all the required nutrients including oxygen and the carbon source. In the continuous method of operation the oxygen source or air is continuously introduced along with continuous introduction of nutrient medium, nitrogen source (if added separately) and alcohol at a rate which is either predetermined or in response to need which can be determined by monitoring such things as alcohol concentration, dissolved oxygen, and oxygen or carbon dioxide in the gaseous effluent from the fermentor. The feed rate of the various materials can be varied so as to obtain as rapid a cell growth as possible consistent with efficient utilization of the alcohol feed, i.e., a high yield of cell weight per weight of alcohol feed charged.

As is known in the art, the feed rate of the alcohol is an important variable to control since in high concentration this material can actually inhibit cell growth and may even kill the microorganism. Therefore, the feed rate of the alcohol is adjusted such that the alcohol is consumed by the microorganism at essentially the same rate as it is being fed to the fermentor. Under preferred operating conditions it is desirable to have little or no alcohol in the effluent which is continuously withdrawn from the fermentor in a continuous type of process. However, satisfactory operation can be achieved with up to about 0.5 percent by volume alcohol concentration in the effluent. For high cell productivity or growth rate, the concentration of alcohol in the feed to the fermentor should be from about 7 percent up to about 50 percent by volume.

For batch or continuous operation of the process of this invention, the concentration of feedstock, e.g., methanol, in the fermentor should be within the range of from about 0.001 up to about 5 percent (v/v) and preferably from about 0.005 up to about 0.5 percent (v/v). It is possible, of course, and may in some instances be desirable, to add the feedstock incrementally to an otherwise typical batch fermentation process.

It is well known in the art that instrumentation is available to measure cell density, pH, dissolved oxygen and alcohol concentration in the fermentor as well as the feed and effluent streams so as to provide a rather complete monitoring of the fermentation process with the instrumentation being adapted to control the input rates so as to optimize the process. The materials fed to the fermentor are preferably subjected to sterilization as is normally done in the art in order to prevent contamination of the desired fermentation mixture by unwanted viable microorganisms.

The effluent removed from the fermentation vessel is subjected to the inventive centrifugation process. The cells can then be further dried by use of drum dryers, spray dryers or the like. The isolated cells can be killed by heat prior to, or preferably during the drying step.

In addition to minimizing the necessary post-treatment of the bacterial cells, the inventive process provides, directly upon fermentation workup, a quality mixed protein material comprising yeast and bacterial protein. Bacteria cells are isolated without the use of additional chemicals, while yeast product is upgraded by bacteria which typically have a higher protein content.

Although the invention has been described herein in conjunction with preferred embodiments thereof, reasonable variations and modifications within the scope of the invention and the appended claims thereto are within the capability of those skilled in the art.

What is claimed is:

1. A process for separating bacteria cells from a first fermentation liquid in which they are contained comprising:
   mixing said first fermentation liquid containing bacteria cells with a second fermentation liquid containing yeast cells to form a mixed product liquid, and
   recovering a mixed product of first and second cells by centrifugation of said mixed product liquid.

2. A process in accordance with claim 1 wherein said mixed product liquid is produced by mixing said first fermentation liquid and said second fermentation liquid in a proportionate amount which provides sufficient second cell content in the mixed product liquid to result in hydrodynamic capture of at least a substantial portion of said first cells during centrifugation.

3. A process in accordance with claim 2 wherein said mixed product liquid comprises from about 10 to 90 percent (v/v) of said second ferementation liquid.

4. A process in accordance with claim 3 wherein said mixed product liquid comprises from about 10 to about 50 percent (v/v) of said second fermentation liquid.

5. A process in accordance with claim 1, 2, 3, or 4 wherein the ratio of the diameter of said second yeast cells to the diameter of said first bacteria cells is within the range of from about 100:1 to about 1:1.

6. A process in accordance with claim 5 wherein the ratio of the diameter of said second cells to the diameter of said first cells is within the range of from about 50:1 to about 2:1.

7. A process in accordance with claim 1, 2, 3, or 4 wherein the ratio of the diameter of said second yeast cells to the diameter of said first bacteria cells is less than about 20:1.

8. A process in accordance with claim 7 wherein the ratio of the diameter of said second cells to the diameter of said first cells is less than about 10:1.

* * * * *